United States Patent [19]

Solow

[11] 4,224,710
[45] Sep. 30, 1980

[54] TOOTHBRUSH FOR THE WHOLE MOUTH

[76] Inventor: Terry S. Solow, 410 Playa Blvd., La Selva Beach, Calif. 95076

[21] Appl. No.: 965,055

[22] Filed: Nov. 30, 1978

[51] Int. Cl.³ .............................................. A46B 13/02
[52] U.S. Cl. .................................. 15/22 R; 128/62 A
[58] Field of Search ................. 15/22 R, 22 A, 22 C, 15/167 A; 128/53, 62 A

[56] References Cited

U.S. PATENT DOCUMENTS

| | | | |
|---|---|---|---|
| 2,771,624 | 11/1956 | Ripper | 15/167 A |
| 3,874,084 | 4/1975 | Cole | 128/62 A |
| 4,137,593 | 2/1979 | Kaster | 15/167 A |

FOREIGN PATENT DOCUMENTS

| | | | |
|---|---|---|---|
| 140409 | 8/1934 | Austria | 15/167 A |
| 2012815 | 9/1971 | Fed. Rep. of Germany | 128/62 A |

*Primary Examiner*—Edward L. Roberts
*Attorney, Agent, or Firm*—Robert G. Slick

[57] ABSTRACT

A power-actuated toothbrush is provided and in its broadest aspects, the toothbrush brushes both sides of a tooth and penetrates into the embrasures. The bristles extend at an angle to the sides of the teeth whereby the bristles of the brush also enter and clean the sulcus area. In preferred embodiments of the invention, the biting surfaces of the teeth are cleaned simultaneously with the sides of the teeth. In other embodiments of the invention, an entire dental arch or even the entire mouth of teeth is cleaned in a single operation.

13 Claims, 20 Drawing Figures

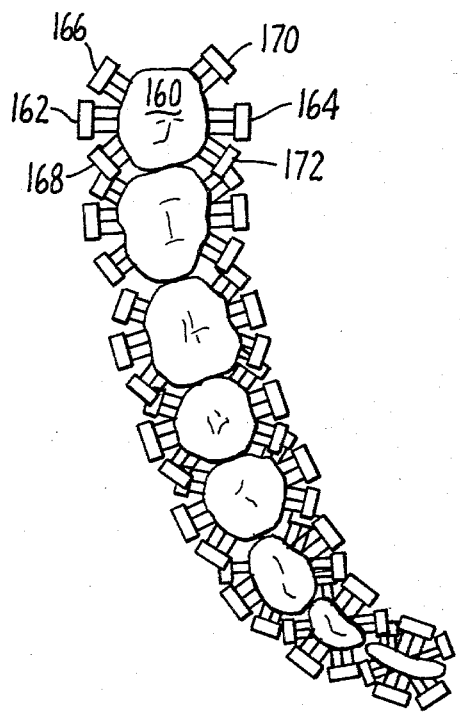
FIG. 13.
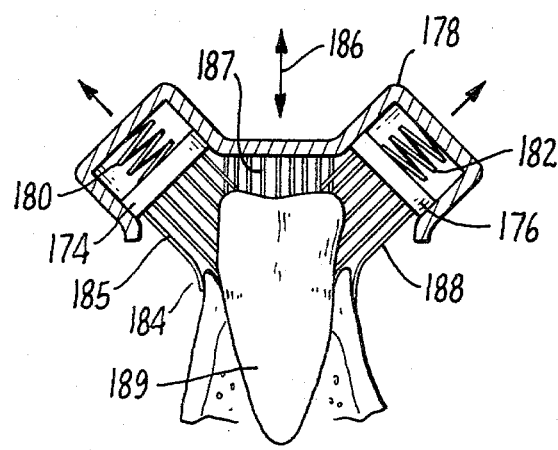
FIG. 14.
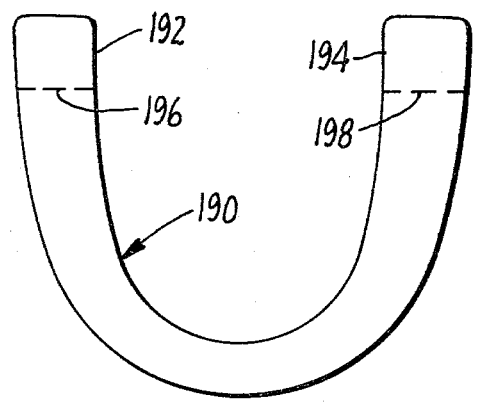
FIG. 15.
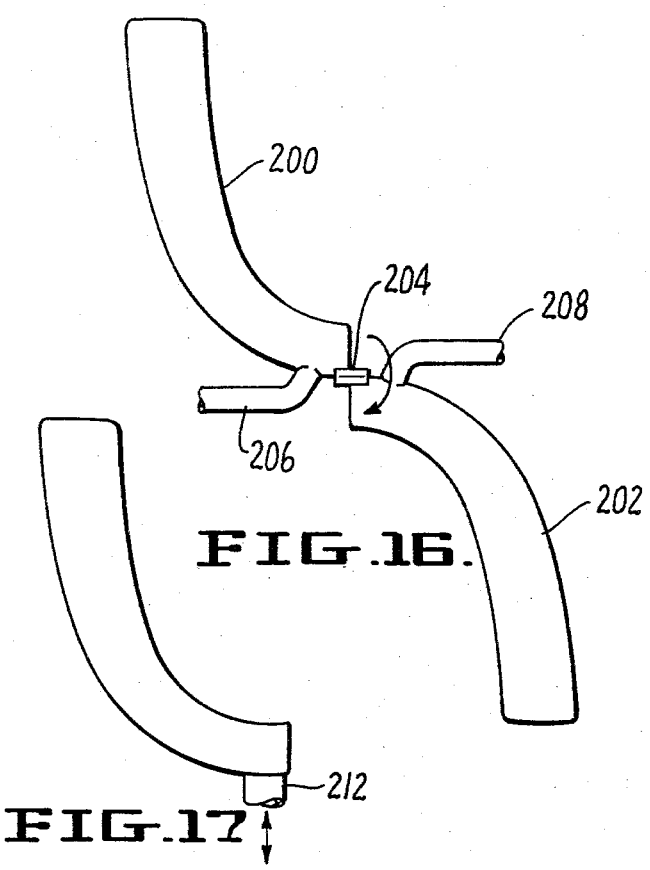
FIG. 16.
FIG. 17.
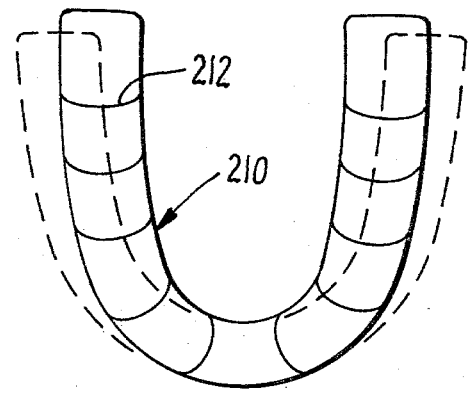
FIG. 18.

TOOTHBRUSH FOR THE WHOLE MOUTH

SUMMARY OF THE INVENTION

The present invention relates to a mechanically driven toothbrush which is particularly adapted for cleaning the teeth including the sulcus area. The angles are selected so that the bristles of the brushes come down on each side of the tooth at an acute angle so that the brittles enter and clean the sulcus area as well as the sides of the tooth and the embrasures. Further, means are provided so that the top or biting surfaces of the teeth are cleaned simultaneously.

In accordance with a preferred embodiment of the invention, the entire mouth of teeth is cleaned with a single operation. In accordance with another embodiment of the present invention, one entire dental arch is cleaned in a single operation. In accordance with still another embodiment of the invention, a quadrant or one half of a dental arch is cleaned in a single operation.

Various means can be used for activating the brushes, such as vibrating rods or strings or reciprocating cams or gears. Preferably, the brushes are caused to vibrate on a plane parallel with the direction of the bristles so that the bristles go in and out of sulcus and embrasures as well as doing a thorough cleaning job on the sides and tops of the teeth. However, as will be later apparent, the most important aspect of the preferred embodiment of the present invention is the fact that the brittles vibrate back and forth along their axis in a "jackhammer" fashion at a selected angle to each tooth. This, coupled with the manner of placing the brush over the teeth, yields superior results because the bristles are brought into contact with the teeth so that the ends of the bristles are not bent in the wrong direction, as they would be if the brush were merely pushed over the teeth. Instead, the bristles remain essentially straight and strike each tooth at a selected angle and thereby also enter the sulcus area for proper cleaning. This will be explained later.

Various means can be used to drive the bristles, and one preferred method is to merely provide a pneumatic actuator coupled with a flexible, hollow tube to a simple compression and vacuum pump that alternately raises and decreases the air pressure in the line, thereby actuating the brushes.

It is preferred that the vibratory action of the brushes be parallel with the direction of the bristles. In another embodiment, the brushes are caused to bear against the teeth in such a manner that the bristles enter the sulcus area, after which various other vibratory directional motions can be employed, such as to and fro, back and forth, up and down, or the like.

Various additional features and advantages of the invention will be brought out in the balance of the specification.

BRIEF DESCRIPTION OF THE DRAWINGS

In the drawings for a part of this application:

FIG. 8 also shows how the toothbrush is held in place by the cleenched upper and lower molars and thereby kept from wiggling about during brushing.

FIG. 13 is a plan view showing how the side brushes can be set at a variety of angles to give a more thorough coverage to all of the tooth surfaces and margins.

FIG. 14 is a view showing how the brushes can be spring-mounted and the entire assembly, rather than individual brushes, may be moved up and down, or perpendicular (i.e. in and out) to the page.

FIG. 15 is a diagrammatic plan view showing how the brush can incorporate removable sections for those people who have no wisdom teeth.

FIG. 16 shows how two quadrants can be mounted together with a locking hinge.

FIG. 17 is a plan view of a single quadrant.

FIG. 18 is a plan view of an embodiment of the invention having sliding hinges to accommodate various shapes and sizes of the dental arch.

DESCRIPTION OF THE PREFERRED EMBODIMENTS

Figure 1:
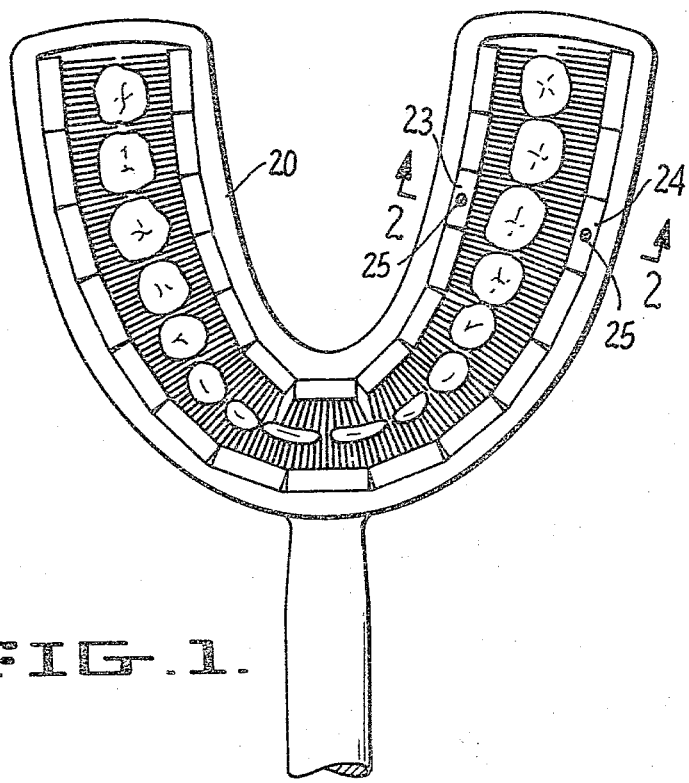
FIG. 1 is a plan view of a toothbrush embodying the present invention wherein the brushes for brushing the top surfaces of the teeth have been removed for clarity of illustration.
Figure 2:
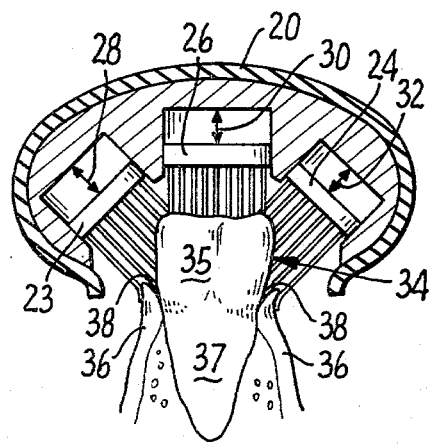
FIG. 2 is a section on the line 2—2 of FIG. 1.

Referring now to FIGS. 1 and 2, there is shown a toothbrush having a casing 20, having a plurality of side brushes, two of which are designated 23 and 24. There is also provided a brush 26 adapted to brush the top surface of a tooth. Means are provided for driving each set of brushes up and down in a direction parallel with the bristles of the individual brush as is indicated by the arrows 28, 30 and 32.

A typical molar is indicated at 34, and surrounding the tooth is the gum 36 with a sulcus or groove 38 approximately at the junction between the crown 35 and the root 37 of the tooth 34. It should be particularly noted that the side brushes 23 and 24 have bristles which not only impinge on the side of the tooth but also enter and thus clean the sulcus area and embrassures, or V-shaped areas between the teeth.

Figure 3:
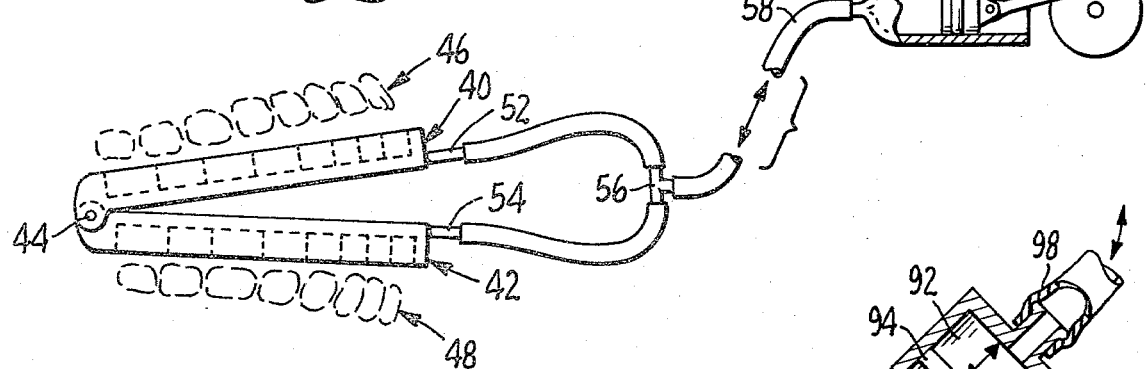
FIG. 3 is a side view, largely diagrammatic, showing a toothbrush for both upper and lower dental arches and a means for actuating the brushes.

As will be later explained in detail, the preferred method of driving the individual brushes is by pneumatic means, using air, namely the application of alternate pressure and vacuum to a chamber attached to the brush elements. Thus, referring to FIG. 3, there is shown a whole-mouth toothbrush having an upper dental arch portion 40 and a lower dental arch portion 42, which are hinged together at 44. These elements are, of course, adapted to simultaneously brush the teeth in the upper dental arch 46 and the lower dental arch 48. Tubing 52 and 54, attached to the upper toothbrush and lower toothbrush units respectively, lead to a tee 56 and a tube 58 to a cylinder 60 having a piston 62 with means 64 adapted to reciprocate the piston. It will be obvious that piston 62 will produce alternating vacuum and pressure in the tubing, and this is used to actuate brush elements as is explained later in detail. Preferably, the individual brush elements are replaceable utilizing known fastening means for the individual elements such as screws 25.

Figures 4, 5A, 5B, 5C, 6:
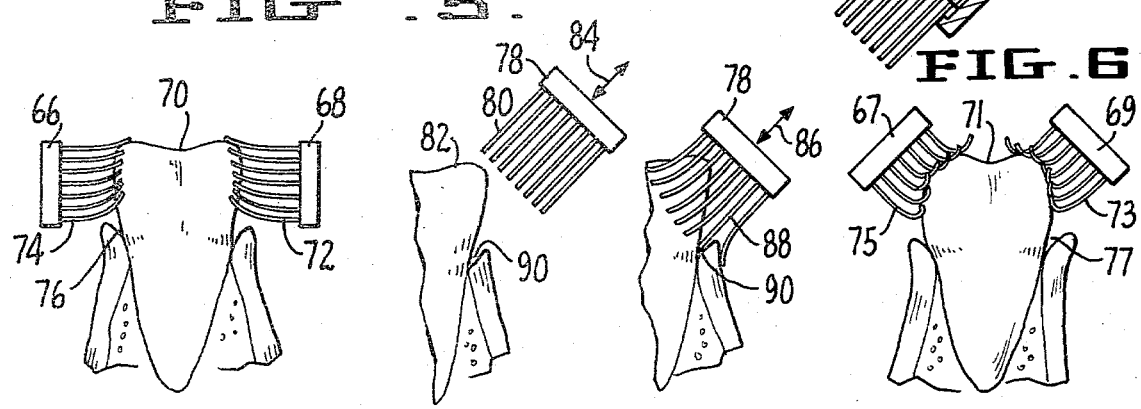
FIG. 4 is an illustration of the inherent problems with prior art attempts at brushing both sides of a tooth at the same time.
FIG. 5A is a partial view showing how the brush element is fully retracted with the bristles fully straight and unbent.
FIG. 5B shows how the brush element of FIG. 5A is brought up against the tooth causing the bristles to impinge on the sides of the tooth and also enter the sulcus area and embrasures.
FIG. 5C is an illustration of what happens to the bristles if the brushes are not fully retracted when a tooth is inserted into the toothbrush. This feature may be used as an automatic toothbrush-centering device.
FIG. 6 is a partial view showing a piston-actuated brush element.

There have been prior art attempts, such as that shown in FIG. 4, to provide a brush that will brush both sides of a tooth simultaneously. Prior art has always vibrated its toothbrush assembly as a complete unit, rather than vibrating the brushes individually. They also selected a vibratory mode that pulls the whole assembly in and out of the mouth. This method does a poor job because the molars are only brushed along their sides and not in the embrasures or in the sulcus region.

To see some of the problems of prior art toothbrushes, refer to FIG. 4. Here the brush elements 66 and 68 have been pushed down over a tooth 70. It will be noted that the bristles, particularly those designated 72 and 74, have not entered the sulcus 76 but instead have been bent upward by the downward movement of the bristles over the tooth.

The dilemma of prior art is two-fold:

1. If they space the brushes 66 and 68 of FIG. 4 far enough apart so that the bristles are straight, the bristles will then not engage the teeth effectively during brushing. This is especially true in the embrasures and the sulcus area.

2. If they space the brushes close together, the brush bristles will bend the wrong way as shown by bristles 72 and 74 of brushes 66 and 68 of FIG. 4. With the bristles bent away from the sulcus area, the embrasures and the sulcus area are thereby not brushed effectively.

As an additional problem, prior art shows the brushes 66 and 68 of FIG. 4 with the bristles in a horizontal position rather than at an angle, as shown in the present invention by brushes 23 and 24 of FIG. 2. The angle of the bristles facilitates entry into the sulcus and the tooth area near the sulcus by the bristles as well as the embrasures. Now, with reference to FIGS. 5A, 5B and 5C, the action of the toothbrush of the present invention is illustrated. To align the toothbrush shown in FIG. 1 properly when inserting it into the user's mouth, all brushes may be forced to their fully-extended positions by external means (not shown). Now, when the toothbrush is pushed over the teeth, the bristles bend the wrong way for proper brushing as shown in FIG. 5C.

This wrong-way bend is corrected as soon as the brushing operation starts and will be explained in more detail shortly. These bent bristles exert a spring-type force on the teeth that very nicely centers the toothbrush properly. The user now clamps his opposing molars onto the rubber bumper 122 shown in FIG. 8. This molar-clenching action holds the entire toothbrush in its proper position and keeps it from wiggling about during the "jackhammer" type brushing action. At the same time, the bladder 124 of FIG. 8 inflates and deflates, jabbing the short bristles into the tops of the molars in a vibratory manner for proper cleaning. Once the power is turned on and the brushes start their movement from fully extended, as shown in FIG. 5C, to fully retracted, as shown in FIG. 5A, the bent bristles straighten out by springing back to their original shape. FIG. 5B shows the next cycle with brush 78 fully extended but now with all bristles properly aligned to clean the sides of the tooth and the sulcus area 90.

FIG. 6 shows one scheme for actuating the brushes. Here a cyclinder 92 is provided with a piston 94 and the bristles 96 are attached to the piston 94. Chamber 92 is connected by means of tube 98 to a source of alternating vacuum and pressure, such as that illustrated in FIG. 3. It will be apparent that the piston 94 will be driven up and down imparting the desired motion to the bristles. Other fluid means can be employed such as hydraulic means.

Figure 7:
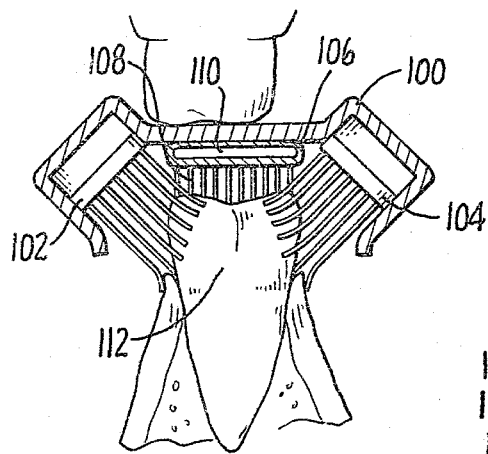
FIG. 7 is a section on the line 7—7 of FIG. 8 wherein the brush element for the top surface of the tooth has relatively short bristles. This reduces the toothbrush height, thereby making the brush more comfortable for the average user.

FIG. 7 which is a modification of the design shown in FIGS. 1 and 2 is particularly adapted for a brush that brushes a single dental arch at a time. Some people may find that it is difficult to open the mouth wide enough and to keep it open wide enough to utilize the brush of FIGS. 1 and 2. Accordingly, in this embodiment of the invention those bristles in contact with the top or biting surfaces of the tooth are very short, permitting a more compact brush than is shown in FIGS. 1 and 2, which therefore does not require as wide a mouth opening. Thus, referring specifically to FIG. 7, the casing 100 has the side brushes 102 and 104 which can be actuated by any desired means. For the top surface of the tooth, the brush 106 is provided with relatively short bristles 108. Further, to make the device compact, the brush is actuated by a bladder arrangement 110 which occupies much less space then the piston arrangement shown by brush 26 in FIG. 2.

Figure 8:
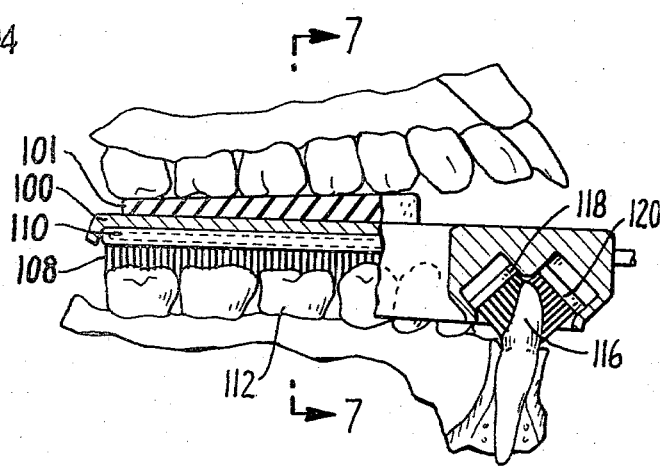
FIG. 8 is a side view, partially in section, showing, among other things, how it is not necessary to employ three brush elements but only two around each tooth in the case of those teeth which are chisel-pointed, i.e. the incisors and canine teeth.

In FIGS. 7 and 8 another modification is shown. This takes advantage of the fact that the molars and bicuspids have flat top surfaces that normally require brushing while the incisors and canine teeth are relatively pointed so that side brushing is all that is required. Thus, referring to FIG. 7, a typical molar 112 is brushed from the top by brush 106 and from the sides by brushes 102 and 104. However, a typical incisor 116 is brushed only by the two side brushes 118 and 120 as shown in FIG. 8.

Figure 9:
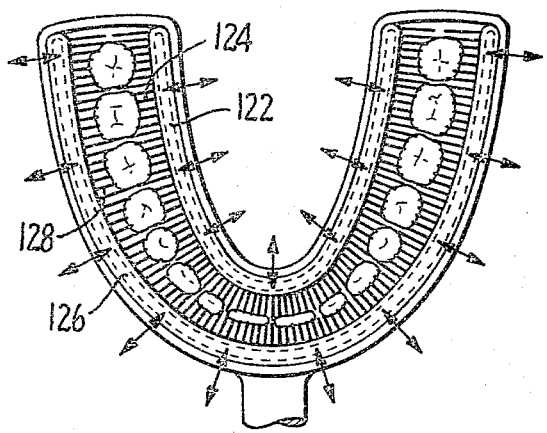
FIG. 9 is a view, similar to FIG. 1, showing how the brushes of the present invention can be actuated using a bladder arrangement.

FIG. 9 illustrates another method of actuating the brush elements. In this view, an inside bladder 122 is connected to the bristles 124, while an outside bladder 126 is connected to the bristles 128. One can apply alternating vacuum and pressure to the bladders utilizing tubes, not illustrated, connecting the bladders with an alternating source of vacuum and pressure such as that shown in FIG. 3.

Figure 10:
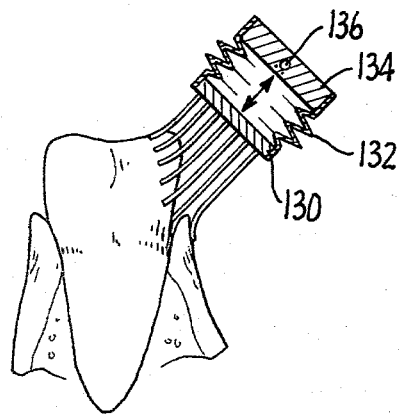
FIG. 10 is a view, similar to FIG. 6, showing how the bristles can be actuated by a bellows.

FIG. 10 illustrates another method of actuating the bristles wherein the back of the brush 130 is connected by means of a bellows 132 to a rear element 134 connected by means of opening 136 to the alternating source of vacuum and pressure to actuate the brush as will be obvious.

Figure 11:
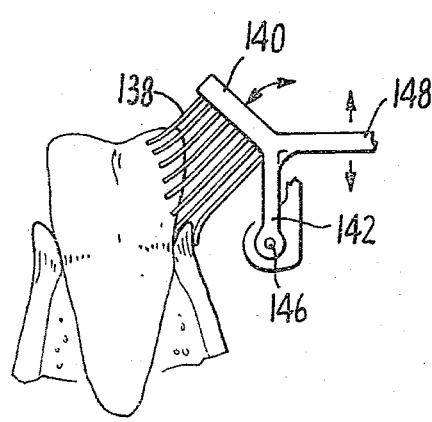
FIG. 11 is a similar view, showing how the bristles can be actuated by means of a rocker arm.

FIG. 11 illustrates still another method wherein the bristles 138 are connected to a backing 140 which is connected to one arm 142 pivoted at a fixed point on the brush holder 146. Lever arm 148 can now be moved up and down by any suitable means. Although this does not give a true back and forth movement to the bristles 138, but instead imparts a slight rotary movement to them, it is near enough to ideal to be completely operative.

Figure 12:
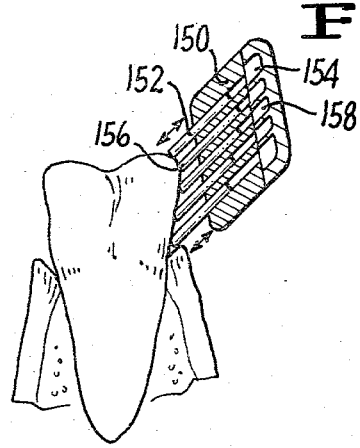
FIG. 12 is a diagrammatic view showing how tufts of bristles can be individually moved rather than moving the entire brush unit.

FIG. 12 illustrates another embodiment of the invention wherein the tufts containing a packet of bristles do not go back and forth as a single brush but instead each tuft packet is oscillated individually. Thus, in the brush holder 150, a bundle of tufts 152 is connected to a chamber 154 and the next adjacent bundle of bristles 156 is connected to a separate chamber 158, and so on. In this manner, the bristles may alternate or be driven in unison, thereby giving a better cleaning action.

In FIG. 13, still another embodiment of the invention is shown when a typical tooth 160 has not only the side brushes 162 and 164 but also has additional brushes 166, 168, 170 and 172. This is a more complicated structure, but it is obvious that it will do a better job of cleaning teeth than merely providing brushes on each side and the top.

FIG. 14 is similar to a section 7—7 out of a toothbrush similar to that shown in FIG. 8, but is different from FIG. 7 in that the top bristles 187 of FIG. 14 are embedded into housing 178 and therefore will not move unless the housing itself moves. When tooth 189 is first inserted into the toothbrush, bristles 185 and 188 bend the wrong way as is shown in FIG. 5C. Brushes 174 and 176 are thereafter fully retracted to alleviate this problem. This new embodiment, whose cross-sectional view is shown in FIG. 14, represents the older concept of vibrating the whole toothbrush and not brushes 174 and 176 individually. Once bristles 185, 187 and 188 are placed properly against the tooth 189 shown in FIG. 14, the whole toothbrush assembly is vibrated as a unit, yet the prior art problems of bristles bent the wrong way, and proper cleaning of the teeth and sulcus area are solved.

Let us proceed on a step-by-step basis in order to make things clear. If a toothbrush similar to FIG. 14 is pressed into place over the teeth, the bristles will bend the wrong way as shown in FIG. 5C. This new embodiment solves this problem by making brushes 174 and 176 of FIG. 14 mechanically retractable on a one-time basis. After inserting the teeth into the toothbrush, the user fully retracts brushes 174 and 176 of FIG. 14 by means (not shown) thereby compressing springs 180 and 182. This act completely disengages the bristles 185 and 188 of FIG. 14 from tooth 189. We now have the condition of straight bristles shown in FIG. 5A. Now, brushes 174 and 176 of FIG. 14 are released and springs 180 and 182 force bristles 185 and 188 against the tooth 189. We now have the condition shown in FIG. 5B where the bristles 88 probe the sulcus area 90. The whole toothbrush of FIG. 14 may now be vibrated, as a single unit, in and out of the page. Although this is a less preferable mode of operation than vibrating the brushes individually, it is lower in cost to produce and satisfactory for many purposes. Additionally, to visualize another more preferable mode of vibration, refer again to FIG. 14. If we now vibrate the whole assembly as a unit in an up-and-down mode as shown by arrow 186, springs 180 and 182 hold bristles 185 and 188 against tooth 189 during the vibration and the tooth and sulcus areas 184 are cleaned. This preferred mode of vibration also cleans the top of tooth 189 more effectively by repeatedly jabbing bristles 187 into the top of the tooth 189.

Other modes and directions of vibration may also be used with this embodiment with varying results in brushing effectiveness.

Many people have lost a third molar or wisdom tooth. In such cases, it is desirable to provide the brush with detachable sections and this is shown diagrammatically in FIG. 15. Thus, the brush is made of a generally crescent shape 190 with the sections 192 and 194 provided with the break lines 196 and 198. With this structure, a user who has lost his wisdom teeth can detach the superfluous sections. Thus, the toothbrush may be made more compact and easier to use.

In FIG. 16, there is shown a structure having two arcuate sections 200 and 202 joined by a locking hinge 204. Each of the sections is provided with a vacuum-pressure hose 206 and 208. In this configuration, the brush can be designed either to brush a single quadrant at a time or two quadrants (upper and lower) at a time. The brush can then be folded over to do the rest of the mouth.

Further, the brush can be made in the form shown in FIG. 17 which is in the configuration of a single quadrant 210 provided with a combination handle and vacuum-pressure tube 212. This makes a very compact and easy-to-use brush.

When a slim toothbrush design is desired, with shorter bristles throughout the toothbrush, the sliding hinge approach shown in FIG. 18 will adjust to various dental arch shapes and sizes. The arch-shaped brush, generally designated 210, is provided with a plurality of sliding hinges 212 whereby it can be adjusted from the position shown in solid lines to that shown in dash lines and vice versa. Also the same slim toothbrush may be used to brush the upper and lower dental arches by simple adjusting means (not shown) that in effect stretches or shrinks the toothbrush via the sliding hinges.

Although various embodiments of my invention have been illustrated, it will be understood that these are nonlimiting examples and that the broad principles of the invention can be applied to toothbrushes differing substantially from the specific embodiments shown without departing from the spirit of this invention.

The bristles are preferably chosen to be soft, pliable and bendable, yet still resilient enough to clean accumulated plaque and not harm the gum tissue or the teeth.

I claim:

1. A toothbrush for brushing both sides of a tooth simultaneously comprising in combination:
    a. a housing of arcuate sectional shape fitting over a row of teeth,
    b. a pair of individual brushes mounted within said housing;
    c. said brushes being spaced from each other and adapted to contact opposite sides of a tooth and being individually movable with respect to said housing;
    d. said brushes having bristles set at an acute angle to the sides of said tooth and being directed toward the sulcus;
    e. means to move said brushes toward and away from each other, to clean the tooth including the sulcus area.

2. The toothbrush of claim 1 having a third brush intermediate between the first two brushes adapted to clean the top of the tooth.

3. The toothbrush of claim 2 having a plurality of paired brushes in side-by-side relationship whereby a plurality of teeth can be cleaned at once.

4. The brush of claim 3 having said brushes arranged in a crescent-shaped housing whereby an entire dental arch can be cleaned at once.

5. The brush of claim 4 wherein two crescent-shaped housings are employed and face in opposite directions whereby the upper and lower dental arches can be cleaned simultaneously.

6. The toothbrush of claim 4 having top brush elements over the bicuspids and molars but having no top element brushes over the canine and incisor teeth.

7. The toothbrush of claim 2 wherein the third brush for the top surface of the tooth has short bristles relative to the bristles of the first two brushes.

8. The toothbrush of claim 2 having a plurality of brushes in a side-by-side relationship, whereby a plurality of teeth can be cleaned at once.

9. The toothbrush of claim 3 wherein each brush includes a plurality of brush elements which are replaceable.

10. The toothbrush of claim 1 wherein the means of paragraph e cause the individual brushes to vibrate in and out, parallel with the line of the bristles.

11. The toothbrush of claim 10 wherein the movement is actuated by pneumatic means including alternately increasing and decreasing the air pressure to a pressure-activated movement means.

12. The toothbrush of claim 11 wherein a liquid is substituted for the air.

13. The toothbrush of claim 1 wherein said brushes called out in paragraph (b) are adapted to simultaneously contact and clean the top of the tooth as well as the sides.

* * * * *